(12) United States Patent
Pandev et al.

(10) Patent No.: US 9,518,916 B1
(45) Date of Patent: Dec. 13, 2016

(54) COMPRESSIVE SENSING FOR METROLOGY

(71) Applicant: KLA-Tencor Corporation, Milpitas, CA (US)

(72) Inventors: Stilian Ivanov Pandev, Santa Clara, CA (US); Alexander Kuznetsov, Mountain View, CA (US); Gregory R. Brady, Campbell, CA (US); Andrei V. Shchegrov, Campbell, CA (US); Noam Sapiens, Cupertino, CA (US); John J. Hench, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/511,810

(22) Filed: Oct. 10, 2014

Related U.S. Application Data

(60) Provisional application No. 61/892,680, filed on Oct. 18, 2013.

(51) Int. Cl.
*G01N 21/25* (2006.01)
*G01N 21/84* (2006.01)

(52) U.S. Cl.
CPC ............ *G01N 21/255* (2013.01); *G01N 21/84* (2013.01); *G01N 2201/06113* (2013.01)

(58) Field of Classification Search
CPC .............................. G01N 21/255; G01N 21/84
See application file for complete search history.

(56) References Cited

U.S. PATENT DOCUMENTS

| | | | |
|---|---|---|---|
| 5,608,526 A | 3/1997 | Piwonka-Corle et al. | |
| 5,859,424 A | 1/1999 | Norton et al. | |
| 6,429,943 B1 | 8/2002 | Opsal et al. | |
| 7,478,019 B2 | 1/2009 | Zangooie et al. | |
| 7,933,026 B2 | 4/2011 | Opsal et al. | |
| 9,291,554 B2 | 3/2016 | Kuznetsov et al. | |
| 2006/0239336 A1* | 10/2006 | Baraniuk | H04L 25/20 375/216 |
| 2010/0021378 A1* | 1/2010 | Rousso | A61B 5/411 424/1.11 |
| 2011/0265578 A1* | 11/2011 | Johnson | G01L 5/0047 73/800 |

(Continued)

OTHER PUBLICATIONS

Ma, Jianwei. "Compressed sensing for surface characterization and metrology." Instrumentation and Measurement, IEEE Transactions on 59.6 (2010): 1600-1615.*

*Primary Examiner* — Kara E Geisel
*Assistant Examiner* — Shawn Decenzo
(74) *Attorney, Agent, or Firm* — Kwan & Olynick LLP

(57) ABSTRACT

Disclosed are apparatus and methods for determining a structure or process parameter value of a target of interest on a semiconductor wafer. A plurality of collection patterns are defined for a spatial light beam controller positioned at a pupil image plane of a metrology tool. For each collection pattern, a signal is collected from a sensor of the metrology tool, and each collected signal represents a combination of a plurality of signals that the spatial light beam controller samples, using each collection pattern, from a pupil image of the target of interest. The collection patterns are selected so that the pupil image is reconstructable based on the collection patterns and their corresponding collection signals. The collected signal for each of the collection patterns is analyzed to determine a structure or process parameter value for the target of interest.

29 Claims, 12 Drawing Sheets

(56) References Cited

U.S. PATENT DOCUMENTS

| | | | |
|---|---|---|---|
| 2012/0069342 A1* | 3/2012 | Dalgleish | G01N 21/47 356/445 |
| 2012/0089365 A1* | 4/2012 | Fay | G01B 11/0675 702/167 |
| 2013/0321810 A1* | 12/2013 | Wang | G01N 21/211 356/369 |
| 2014/0172394 A1 | 6/2014 | Kuznetsov et al. | |
| 2016/0139032 A1 | 5/2016 | Rampoldi et al. | |

* cited by examiner

COMPRESSIVE SENSING FOR METROLOGY

CROSS-REFERENCE TO RELATED APPLICATIONS

This application claims the benefit of prior application U.S. Provisional Application No. 61/892,680, filed 18 Oct. 2013 by Stilian Ivanov Pandev et al., which application is herein incorporated by reference in its entirety for all purposes.

TECHNICAL FIELD OF THE INVENTION

The present invention relates generally to methods and systems for semiconductor metrology and, more specifically, to using multiple wavelengths, polarizations, and angle-resolved measurements.

BACKGROUND

Photolithography or optical lithography systems used in the manufacture of integrated circuits have been around for some time. Such systems have proven extremely effective in the precise manufacturing and formation of very small details in the product. In some photolithography systems, a circuit image is written on a substrate by transferring a pattern via a light or radiation beam (e.g., UV or ultraviolet light). For example, the lithography system may include a light or radiation source that projects a circuit image through a reticle and onto a silicon wafer coated with a material sensitive to irradiation, e.g., photoresist. The exposed photoresist typically forms a pattern that after development masks the layers of the wafer during subsequent processing steps, as for example deposition and/or etching.

Due to the large scale of circuit integration and the decreasing size of semiconductor devices, the reticles and fabricated devices have become increasingly sensitive to critical dimension (CD) variations, as well as other critical parameter variations such as film thickness and composition, etc. These variations, if uncorrected, can cause the final device to fail to meet the desired performance due to electrical timing errors. Even worse, these errors can cause final devices to malfunction and adversely affect yield.

In one metrology technique, critical dimension is measured by scanning electron microscope CD-SEM images at each location on the wafer and examining each image for pattern quality. This technique is time consuming (e.g., several hours). Other techniques have their own disadvantages.

In view of the foregoing, improved apparatus and techniques for determining structure or process parameters of a printed pattern are desired.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method of determining a structure or process parameter value of a target of interest on a semiconductor wafer is disclosed. A plurality of collection patterns are defined for a spatial light beam controller positioned at a pupil image plane of a metrology tool. For each collection pattern, a signal is collected from a sensor of the metrology tool, and each collected signal represents a combination of a plurality of signals that the spatial light beam controller samples, using each collection pattern, from a pupil image of the target of interest. The collection patterns are selected so that the pupil image is reconstructable based on the collection patterns and their corresponding collection signals. The collected signal for each of the collection patterns is analyzed to determine a structure or process parameter value for the target of interest.

In a specific implementation, the signal collected for each of the collection patterns is collected from a single point or pixel detector. In a further aspect, each signal collected from the single point or pixel detector is a sum or average of a plurality of intensities that the spatial light beam controller samples from the pupil image. In a further embodiment, the method includes reconstructing the pupil image based on the collection patterns and their corresponding collection signals, and the pupil image of the target of interest is sparse when transformed to a particular domain of transformation elements $\Psi$. The pupil image can also be represented by $\Psi\alpha$, with $\alpha$ being weights, and the pupil image is reconstructed by an $l_1$ optimization. In one example, the particular domain corresponds to a transform to a plurality of Zernike polynomial basis images. In another example, the particular domain corresponds to a DFT (discrete Fourier transform), DCT (discrete cosine transform), DST (discrete sine transform), FFT (fast Fourier transform), DWT (discrete Wavelet transform), or other a Wavelet transform.

In an alternative embodiment, a representative set of pupil images are obtained from a plurality of test structures that were fabricated or simulated with known process variations. Basis images for a plurality of possible collection patterns that are most related to the known process variations are extracted from a large set of basis images that are generated for the representative set of pupil images. The extracted basis images are used to define the collection patterns for the spatial light beam controller.

In one implementation, the spatial light beam controller includes a plurality of pixels that are turned on or off for spatially sampling the pupil image to form each collection pattern. In another aspect, the spatial light beam controller includes a plurality of pixels that have a plurality of analog values for spatially sampling the pupil image to form each collection pattern. In an alternative implementation, a plurality of illumination patterns are defined for a second spatial light beam controller positioned at an illumination plane of the metrology tool. In a further aspect, the operations for defining, collecting, and reconstructing are repeated for each of a plurality of combinations of wavelength ranges, polarization states, and/or illumination patterns. In another aspect, the structure or process parameter value is determined by a model for predicting a structure or process parameter value based on a plurality of collected signal values. In another embodiment, the structure or process parameter value for the target of interest is determined without reconstructing the pupil image.

In an alternative embodiment, the invention pertains to a system for inspecting or measuring a specimen. This system comprises an illuminator for generating illumination and illumination optics for directing the illumination towards a target of interest on a semiconductor wafer. The system also includes collection optics for directing a plurality of signals from the particular structure to a sensor (for collecting the plurality of signals from the target of interest) in response to the illumination, and the collection optics comprise a spatial light beam controller for controlling a spatial profile of a pupil image of the metrology system. The system further includes a controller configured for performing any of the above described operations.

In an alternative method embodiment, one or more collection patterns are defined for a spatial light beam controller positioned at a pupil image plane of a metrology tool, and each collection pattern is defined based on a plurality of coefficients of a model for predicting a corresponding structure or process parameter value for a target of interest. For each collection pattern, a signal is collected from a sensor of the metrology tool, and each collected signal represents a combination of a plurality of signals that the spatial light beam controller samples, using each collection pattern, from a pupil image of the target of interest. A value of each collected signal is reported for each of the collection patterns as a corresponding structure or process parameter value for the target of interest.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Figure 1:
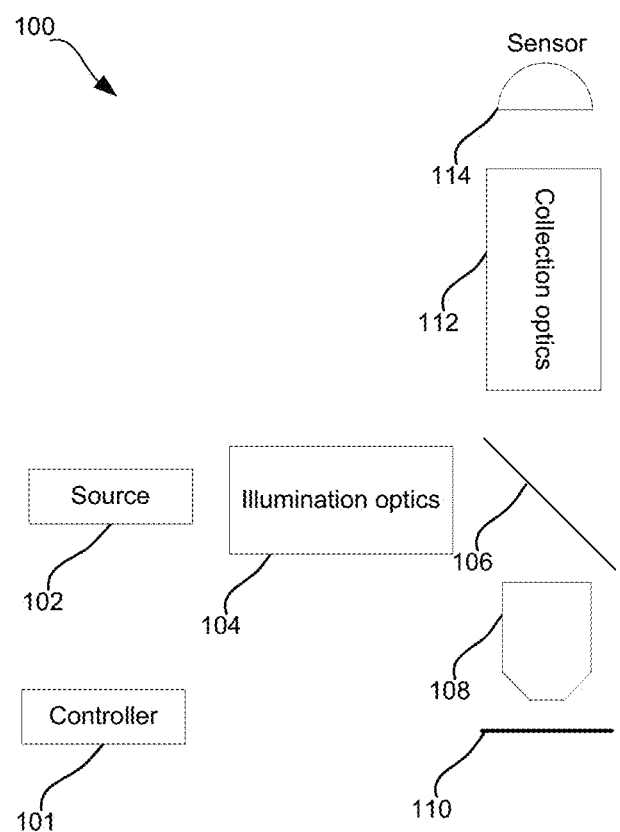
FIG. 1 is a simplified diagram of a metrology system.

FIG. 1 is a simplified diagram of a metrology system 100. In a general example, a metrology tool may comprise an illumination system which illuminates a target, a collection system which captures relevant information provided by the illumination system's interaction (or lack thereof) with a target, device or feature, and a processing system which analyzes the information collected using one or more algorithms. Metrology tools can generally be used to measure various radiation signals pertaining to structural and material characteristics (e.g., material composition, dimensional characteristics of structures and films such as film thickness and/or critical dimensions of structures, overlay, etc.) associated with various semiconductor fabrication processes. These measurements can be used to facilitate process controls and/or yield efficiencies in the manufacture of semiconductor dies.

The system 100 generally includes a source 102 generating radiation (or electromagnetic waveforms) and illumination optics 104 that may include lenses, mirrors, concave, convex, parabolic mirrors, polarization components (polarizer(s), waveplates or other), apertures, shutters, apodizers and/or other optical and/or electro-optical components. The illumination optics 104 has the role of delivering the radiation to the wafer 110 in a manner that best serves the measurement mode of the system 100. For example, the illumination optics 104 may include a set of lenses and apertures to introduce a diffraction limited spot on the wafer 110 at a specific numerical aperture (NA). In another example, the illumination optics 104 includes a polarizer to control the polarization incident on the wafer 110. The polarizer may be static or rotatable. The system 100 may also include an objective 108 in form of, for example, a high NA objective (e.g. 0.9, 0.93, 0.95 or even higher). The system 100 may also include a beam splitter 106 for reflecting the illumination light towards the sample 110 and transmitting the output light that is emitted from the sample 110 towards the collection optics 112. Either or both the illumination and collection optics may include any number of beam splitters, depending on the particular configuration of the system components.

The collection optics 112 may be arranged to perform a transformation to introduce the desired signal onto sensor 114. The sensor 114 may include a single detector, an array of detectors (as, for example, in a charge-coupled device (CCD) camera, a complementary metal oxide semiconductor (CMOS) camera), a spectrometer, an avalanche photodiode, photomultiplier tube (PMT), and/or other detector type for collecting signals from the sample. The detector may be configured to detect small numbers of photons.

The pupil image includes signals that are obtained at different angles of incidence (or azimuth angle) from the target area. Since a typical pupil image for a semiconductor target area is typically smooth, a transformation of such pupil image into particular domains results in a sparse image. Compression techniques may be implemented with respect to sparse images. Accordingly, certain embodiments of the present invention pertain to a compressive sensing system. Such a system includes at least one spatial beam control device in either: the illumination arm, the collection arm or both. This spatial beam control may be, but is not limited to, one of the following: a spatial light modulator (SLM), which is a device that is used to variably control the light amplitude and/or phase spatial distribution (e.g. by using a micro mirror array device (digital or analog), a liquid crystal spatial light modulator device, a liquid crystal on Si (LCOS) device), and/or a set of movable (e.g., translatable or rotatable) masks (e.g., apertures or apodizers). The spatial beam control device can also be in the form of one or more deformable mirrors, which are available from Boston Micromachines of Cambridge, Mass.

In certain embodiments, the acquired signals in the sensor 114 are a series of measurements corresponding to multiple, random or predetermined spatial beam control patterns. These signals can be defined by the system mode of operation and the type of sensor that is used in the measurements. In one embodiment, the set of patterns along with the acquired signals can then be used to reconstruct images and/or other parameters, by means of algorithms. Various techniques or algorithms can then be used to extract the desired target or wafer characteristics. Various processes may also or alternatively be implemented to enable the extraction of target and wafer characteristics directly from the measured signals and their corresponding patterns (some ways described in the background section).

Figure 2:
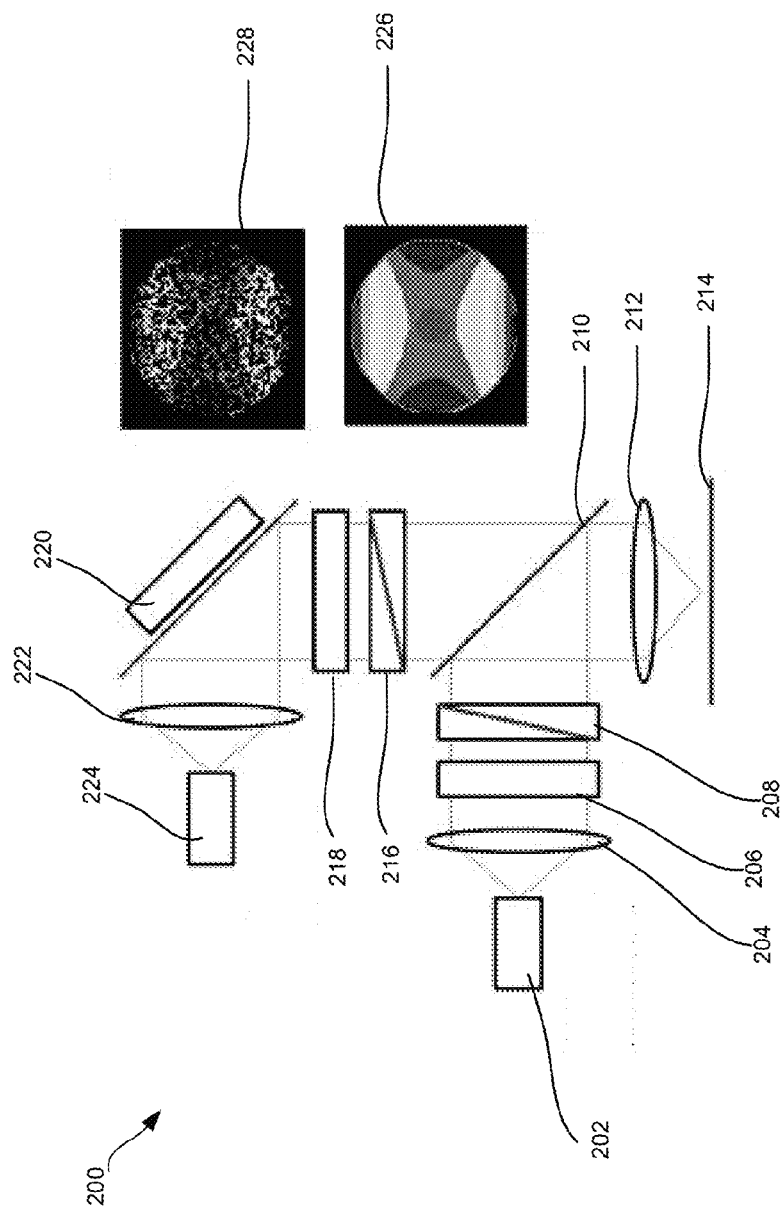
FIG. 2 is a diagrammatic representation of an angle resolved system, in which a broadband-light source is used for illumination, for implementing techniques of the present invention.

FIG. 2 is a diagrammatic representation of an example angle resolved system 200 for implementing techniques of the present invention. As shown, the system 200 may include an illumination source 202 for generating illumination light. In this example, the light source 202 can be a broadband light source. Examples broadband sources include an arc lamp, an electrode-less lamp, a supercontinuum source, such as a broadband laser source available from NKT Photonics Inc. of Morganville, N.J. The metrology system may also include a fast feedback to the light source for stabilizing its power and wavelength. Output of the light source can be delivered via free-space propagation, or in some cases delivered via optical fiber or light guide of any type.

The system 200 may also include any suitable illumination optics, including lens 204, polarizer 206, waveplate 208, beam splitter 210, and objective 212 for directing the illumination beam towards the sample, such as wafer 214. The polarizer controls the polarization state of the illumination beam that is directed towards the sample 214.

The system further includes collection components, such as waveplate 216, analyzer 218, SLM 220, and lens 222, which are arranged for receiving and conditioning the output beam that is emanating from the sample 214, in response to the incident beam. The system 200 may include other collection components, such as one or more shutters to block portions of the output beam or sampled beam. The analyzer may be static or rotatable to analyze radiation from the sampling beam. The collection components are further arranged to direct the output beam towards a sensor, such as single pixel camera 224. In the illustrated embodiment, SLM 220 may be configurable to sample the pupil image by controlling the amplitude and/or phase of the output light. Any suitable spatial light beam controller may be used to spatially sample the output light as further described herein.

Figure 3:
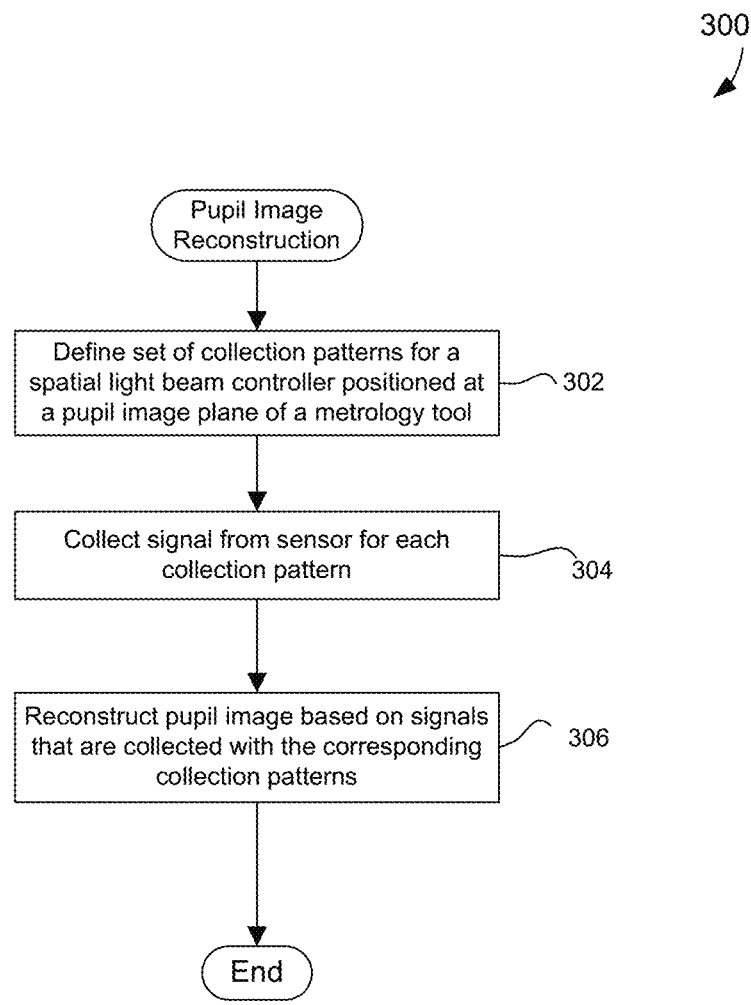
FIG. 3 is a flow chart illustrating a procedure for reconstructing pupil images in accordance with one embodiment of the present invention.

FIG. 3 is a flow chart illustrating a procedure 300 for reconstructing pupil images in accordance with one embodiment of the present invention. Initially, a set of collection patterns may be defined in operation 302. The collection patterns are generally defined for a spatial light beam controller that is positioned at a pupil image plane of a metrology tool. For instance, SLM 220 is set up to sample the output light at a plurality of SLM patterns at the pupil plane. As shown, an example pupil image 226 of the sample 214 may be formed at the pupil plane prior to sampling of the output light by the SLM 220. When pupil image 226 is sampled by the SLM at the pupil plane, sampled image 228 results.

Referring to FIG. 3, a signal may be collected from the sensor 224 for each collection pattern in operation 304. For instance, the sampled light from each SLM pattern is focused to a single point, where a sensor 224 collects the integrated light from the sampled pupil image. As shown, the sensor 224 may be a spectrometer if the spectrum of the measurement is of interest. If the system is used in a low light modality, a highly sensitive, low noise point detector, such as a photomultiplier tube (PMT) or avalanche photodiode may be used to collect the light. In this embodiment, all of the photons are sensed and processed electronically by a single point detector.

One result of single point detection is that the noise introduced is that of a single detector. In an array detector, the total number of photons is divided over a large number of detector elements, each with their own associated noise. Thus, there is a significant noise benefit to integrating the signal on a point detector that enables measurement at much lower light levels than with an array detector. This reduces the damage to photoresist structures by the measurement and allows for the use of a lower brightness illumination sources.

Intensities measured by the sensor 224 correspond to the sum or average of the intensities reflected by the pixels of the pattern of the SLM 220 that are "turned on" or sampled for a particular sample. The pupil image can be reconstructed based on the signals that are collected with the corresponding collection patterns by performing a compression sensing process in operation 306. The above process can be repeated for each different wavelength or wavelength range, polarization state, etc.

Figure 4A:
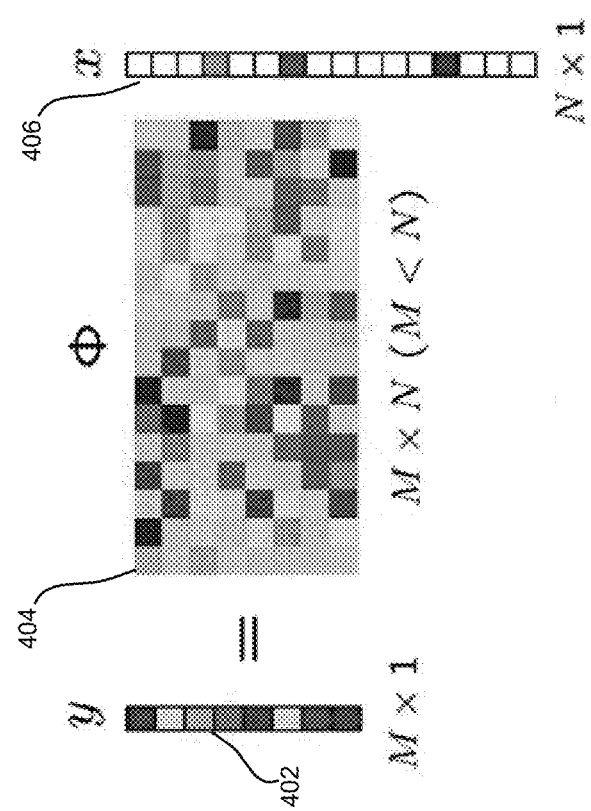
FIG. 4A illustrates principals of a compression technique in accordance with one example implementation of the present invention.

FIG. 4A illustrates principals of a compression technique in accordance with one example implementation of the present invention. Measurement array y (402) has a size of M×1 and represents M number of y measurements obtained from single point detector 224. Each measurement was obtained from a sensor for a particular sampling pattern. Said in another way, each measurement also corresponds to an inner product or correlation between a signal x and a sensing function φ. The pupil image x and measurements array y are each vectorized into a one dimensional array.

The sensing function is a model or description of the sensing system. The sensing function φ is represented by array 404 having a size M×N. Each row of the sensing function φ represents a setting or sampling pattern of the SLM 220. For instance, each pixel of the SLM can be turned on or off or be set to an analog value (e.g., between 0 and 1). The x array includes all N pixels of the pupil image. Each element of each row of the sensing function ϕ is applied to a single pixel or area of the signal x or the pupil image, which is represented by array 406. As shown, the pupil image array 406 has a size N×1, which corresponds to the pixels of the pupil image to which different rows of the sampling pattern ϕ are applied to obtain measurements y.

The sampling patterns ϕ (404) and corresponding y measurements (402) are known and can be used to reconstruct the pupil image x (406). A compression sensing technique takes advantage of the pupil image x (406) being sparse in a particular domain, which allows the pupil image to be reconstructed using the undetermined system of y measurements and known sampling patterns ϕ. This relationship can be represented by the following equation (1):

$$y=\phi x \quad \text{Equation (1)}$$

Figure 4B:
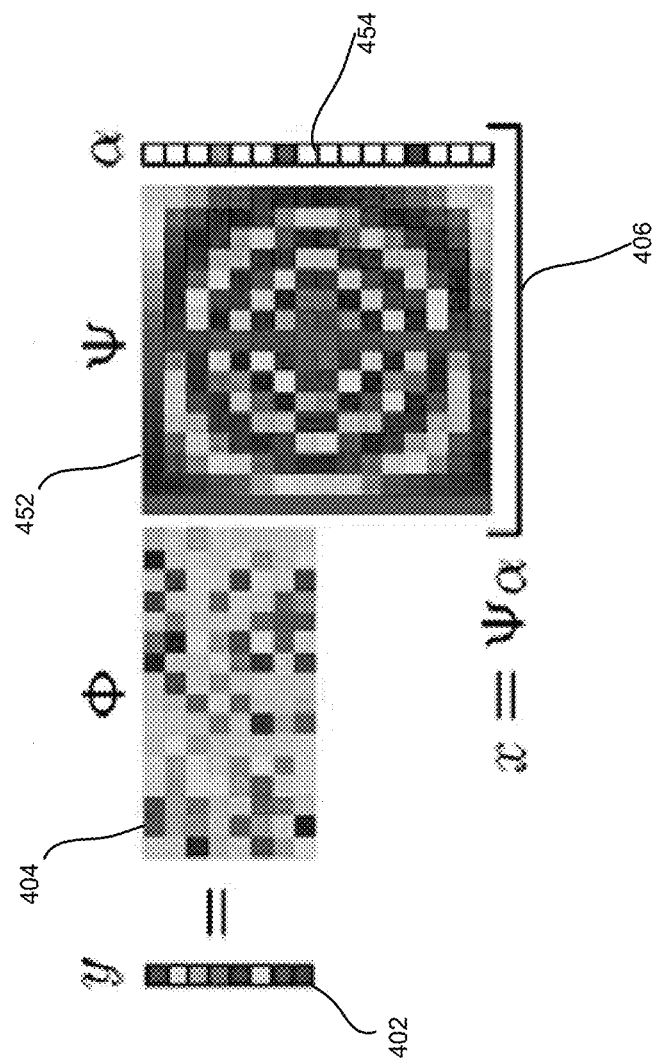
FIG. 4B is a diagrammatic representation of a sparsity quality of a domain into which the pupil image is transformed in accordance with one example implementation of the present invention.

FIG. 4B is a diagrammatic representation of a sparsity quality of a domain into which the pupil image is transformed in accordance with one example implementation of the present invention. Although the original signal or pupil image x is not sparse, the signal x is sparse in at least one domain Ψ. The signal x can be represented as a weighted linear combination of basis images or $\Psi_a$, where α is an array of weights (454) and Ψ is a linear combination of transformation elements (452). Equation (1) can be written as $$y=\Phi x=\Phi\Psi\alpha=\Theta\alpha \quad \text{Equation (2)}$$

where $\Theta=\Phi\Psi$ is an M×N matrix.

The sparse representation of the pupil image can be recovered by an $l_1$ optimization:

$$\hat{\alpha}=\text{argmin } \|\alpha'\|_1 \text{ such that } \Theta\alpha'=y \quad \text{Equation (3)}$$

where α' is one of the solutions of Equation (2), and $\hat{\alpha}$ is the optimal solution of Equation (2) recovered by an $l_1$ optimization, which minimizes $l_1$-norm.

Then the pupil image can be recovered by x=Ψα.

Figure 5:
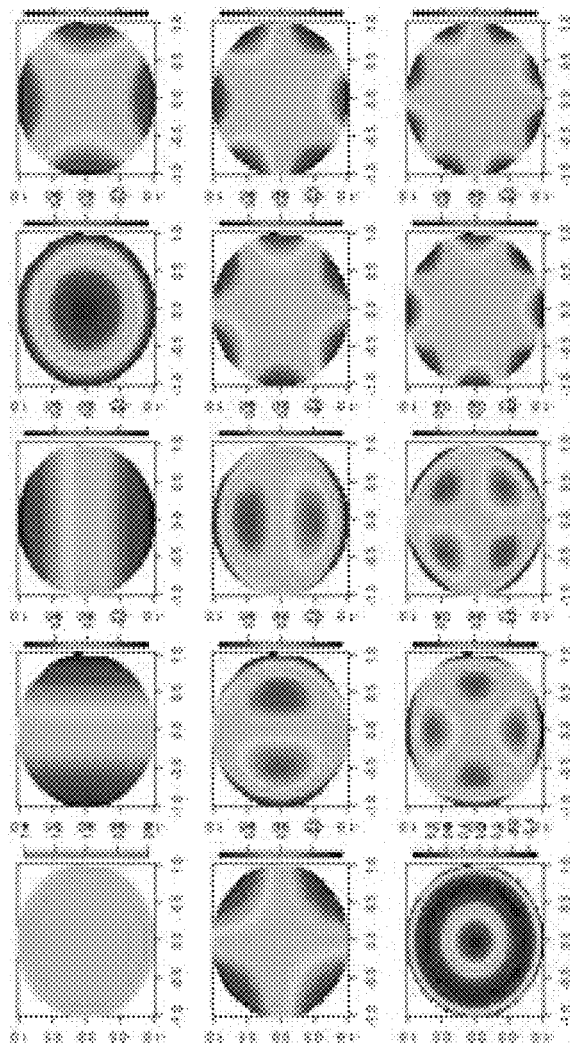
FIG. 5 represents a set of Zernike polynomial basis images that can be used for reconstructing the pupil image in accordance with one embodiment of the present invention.

The number of measurements M depends on the sparseness of the pupil image signal in Ψ domain. The signal x is K-sparse if it is a linear combination of only K basis vectors with only K coefficients of the α vector being non-zero. In order to recover the K-sparse signal, only M≥cK log(N/K) measurements, corresponding pupil images, and corresponding sampling patterns are needed. FIG. 5 represents a set of Zernike polynomial basis images that can be used for reconstructing the pupil image in accordance with one embodiment of the present invention. Other bases and transformations that can be used for the reconstruction of the pupil image may include, but are not limited to, DFT (discrete Fourier transform), DCT (discrete cosine transform), Wavelet transform.

In a preferred embodiment, the bases are measurement sample dependent and are obtained by analyzing the pupil images produced by a test sample and process applied to it. In certain processes such as lithography, only the set of sample variation and signal variations that are possible within the process window significantly increase the sparsity of the signal and, hence, reduce the number of coefficients needed to reconstruct the pupil image.

Figure 6:
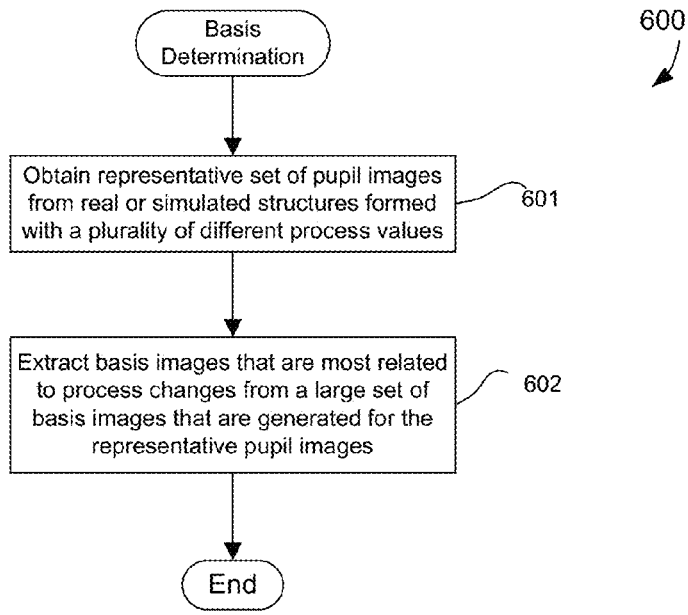
FIG. 6 is a flow chart illustrating a procedure for determining optimal basis from representative pupil images in accordance with one embodiment of the present invention.

FIG. 6 is a flow chart illustrating a procedure 600 for determining optimal basis from representative pupil images in accordance with one embodiment of the present invention. Initially, a representative set of pupil images may be obtained from actual or simulated structures that were formed using a plurality of different process values in operation 601. That is, the images can be simulated or can be collected from actual fabricated samples (FEM wafer). Images that are collected from a particular inspection tool will more accurately include the optical effects from the tool itself, while the simulated images may be generated as "ideal" images without optical effects from the inspection tool. Of course, the optical effects from the particular tool may also be incorporated into the simulated images.

Basis images (or sampling patterns) that are most related to process changes may then be extracted from the representative pupil images in operation 602. In one embodiment, sampling patterns that are most sensitive to process change are extracted. For example, a set of sampling patterns may be extracted as providing more information related to focus and dosage change.

Any suitable feature extraction technique may be implemented so as to extract a set of optimum basis images with the best information pertaining to changes in process parameters, such as focus/dose. An operator of the metrology tool may select the set of sampling patterns to be extracted by assessing different sampling patterns through trial and error to determine a best set that provides a change trajectory with respect to the focus that is similar to a change trajectory in a characteristic of the fabricated structure as a function of focus. An automated analysis of different sampling patterns may be executed based on optimization of some criteria, such as selecting the set of sampling patterns that form a set of parabolic shapes (for the different exposures) as a function of focus with minimum noise. Additionally, a combination of wavelength ranges may be selected so as to cancel any effects to the signal caused by targets in lower layers. For instance, certain wavelengths may result in a circular contour pattern with respect to the focus and dose wafer sites, as opposed to parabolic shaped contours for wavelengths that are insensitive to underlying structures. The wavelength ranges that are found to be sensitive to underlying layer targets may be deselected from being used as an extracted feature.

Example automated feature extract techniques include Principal Component Analysis (PCA), Independent Component Analysis (ICA), Local Linear Embedding (LLE) algorithm, etc. Any number of principal components may be selected based on the particular requirements of the application. For instance, the first 30~40 principal components, as determined via PCA, may be used. In a preferred embodiment, 10 to 20 principal components are utilized. In yet another example, the output from another feature extraction tool, such as kernel PCA, ICA or LLE, may be used.

In a PCA embodiment, the extracted feature corresponds to a transformation of the measured dataset onto a different coordinate system and selection of a particular dimension (or direction or projection direction) of such new coordinate system along which the transformed dataset has the most variation, which provides the most information with respect to process parameter changes. Said in another way, a dataset may be created with different basis sets that can be defined as the variables (columns) for different focus/dose target sites or samples (rows). The first principal component corresponds to a transformed direction or dimension of the PCA-transformed dataset that is found to have the most variation. The second principal component has the second most variation, etc.

Figure 7A:
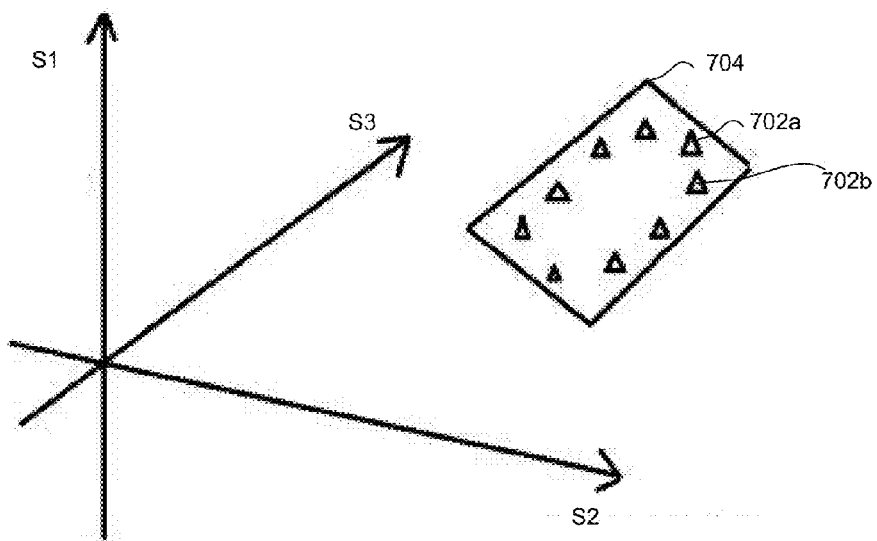
FIG. 7A is a plot of a simplified signal dataset as a function of three basis sampling patterns in accordance with one embodiment of the present invention.

FIG. 7A is a plot of a signal dataset as a function of three basis sampling patterns in accordance with one embodiment of the present invention. As shown, the sample dataset has three dimensions corresponding to sampling patterns S1, S2, and S3. Each sampling pattern (S1~S3) may correspond to a different set of one or more "turned on" (or different analog values) positions in the SLM, and the dataset is plotted relative to these different sampling patterns. For instance, S1 corresponds to a first pixel position being on; S2 corresponds to a second pixel position being on, etc. Any sampling pattern can correspond to a combination, such as the first and second pixel both being turned on.

The dataset includes data points 702a and 702b that correspond to signal measurements with respect to the different sampling patterns at two different focus sites. For instance, a first focus site can result in particular set of intensity values at each turned on pixel of the spatial controller, and a second focus site can result in a second set of intensity values for each turned on pixel. If S1 corresponds to only a first pixel position being turned on, the first pixel may still have a same value for each of the different focus sites. Conversely, S1 can have widely different intensity values for the set of focus sites.

In the illustrated example, sampling pattern S1 is associated with a constant value for all the data points. That is, the data sets reside in a plane that is perpendicular to the S1 dimension. In one application, S1 may represent a particular sampling pattern that does not result in any measured signal variation for different focus sites.

Figure 7B:
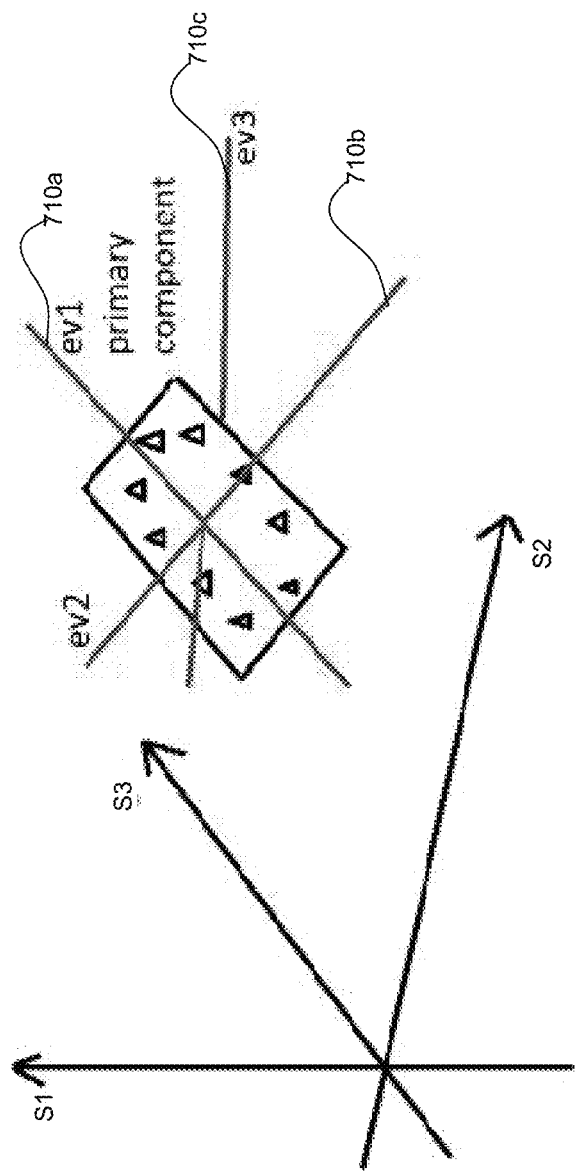
FIG. 7B illustrates the three eigenvectors for the three dimensional dataset of FIG. 7A in accordance with a specific implementation of the present invention.

FIG. 7B illustrates the three eigenvectors for the three dimensional dataset of FIG. 7A in accordance with a specific implementation of the present invention. As shown, the dataset has three eigenvectors ev1 (710a), e2 (710b), and e3 (710c). Each of the eigenvectors also has an eigenvalue that corresponds to the amount of variance in the dataset with respect to such eigenvector. For instance, the principal eigenvector e1 (710a) is associated with the most dataset variance. In contrast, the eigenvector e2 (710b) has significantly less dataset variance, and the eigenvector e3 (710c) has zero dataset variance. The top most eigenvalues that correspond to the highest dataset variance can be selected and used to determine the basis components and coefficients for programming the spatial light beam controller. Eigenvalues determine the strength of corresponding eigenvectors. In the case of the spatial light beam controller, each eigenvalue defines the strength of particular pattern (represented by eigenvector)

Figure 8A:
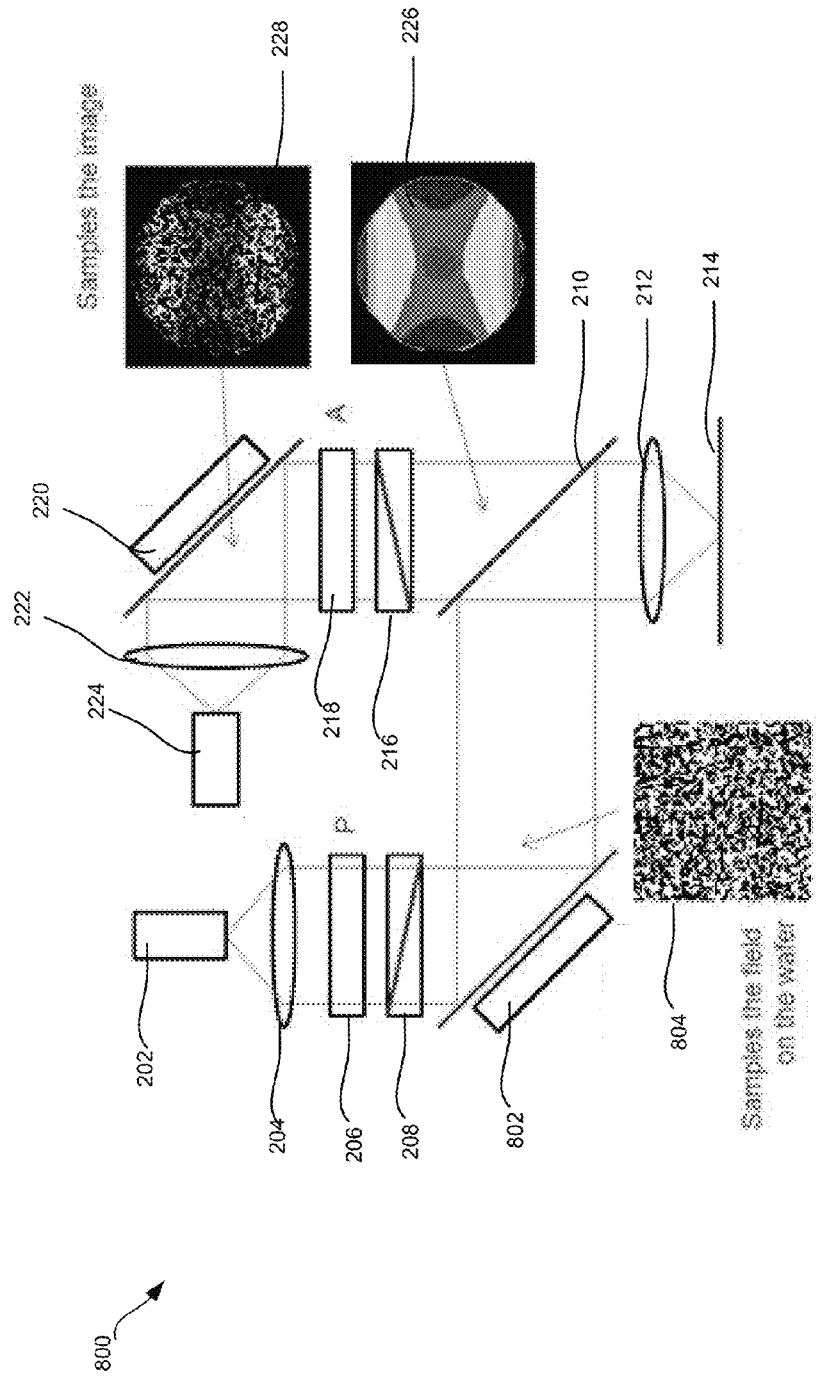
FIG. 8A is a diagrammatic representation of a compressive system having a broadband-light source and an additional DMD at the illumination side, in accordance with an alternative embodiment of the present invention.

FIG. 8A is a diagrammatic representation of a compressive system 800 having a broadband-light source and an additional SLM at the illumination side, in accordance with an alternative embodiment of the present invention. This system can have similar components, with the same reference numbers, as the system of FIG. 2. As shown, the light from the light source 202 is reflected from a pattern of the illumination SLM 802 and projected on the wafer sample. For instance, SLM 802 can have illumination pattern 804.

An illumination-side SLM may be used for any suitable purpose. For example, certain target areas may contain a plurality of different types of targets, such as device-like targets, CD grating targets, high density array targets, etc. Different illumination patterns may be used isolate different individual targets within the same field. Additionally, different SLM patterns may be used for different types of targets. For example, symmetric SLM patterns will generally perform better for symmetric targets. In an alternative example, the illumination SLM may be used to sample the whole field, and the relations between images and field areas may be reconstructed from a series of measurements with the illumination SLM patterns and then using compressive sensing techniques. In another technique, a shutter may be used to randomly modulate the light beam and reconstruct the amplitudes of the harmonics of the collected signals so as to reconstruct one or more pupil images representing different polarization states.

Figure 8B:
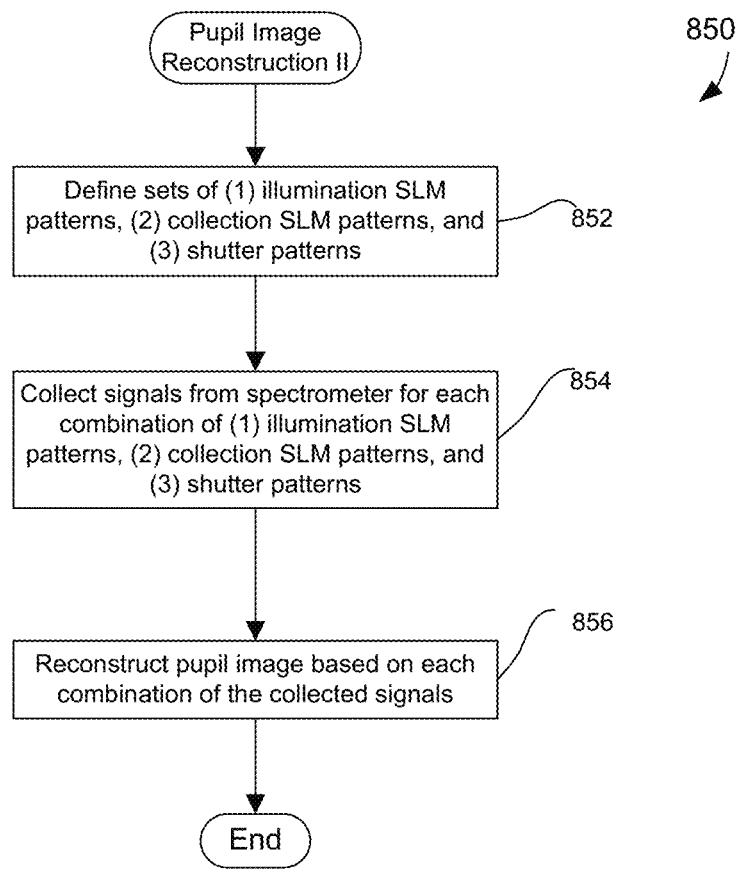
FIG. 8B is a flow chart illustrating a procedure for reconstructing a pupil image using the system of FIG. 8A in accordance with an alternative embodiment of the present invention.

FIG. 8B is a flow chart illustrating a procedure 850 for reconstructing a pupil image using the system of FIG. 8A in accordance with an alternative embodiment of the present invention. Initially, one or more sets of (1) illumination SLM patterns, (2) collection SLM patterns, and (3) shutter patterns may be defined in operation 852. For example, a specific illumination SLM pattern may be used to optimize target illumination, a specific collection SLM pattern may be chosen to encode the signal, and a specific shutter pattern may be used to block certain light rays. Signals may then be collected from the spectrometer for each combination of (1) illumination SLM patterns, (2) collection SLM patterns, and (3) shutter patterns may be defined in operation 854. The pupil image may the reconstructed for each combination of collected signals in operation 856. If a spectrometer is used for the sensor (e.g., 202), the reconstruction can be performed for each wavelength that is resolved by the spectrometer, resulting in a hyperspectral image cube (or cylinder, since the pupil image is typically round) with a complete spectrum measured at each spatially resolved pixel. The process of FIG. 8B can be repeated for each of a plurality of combinations of polarization states, wavelength ranges, illumination patterns, etc.

Figure 9:
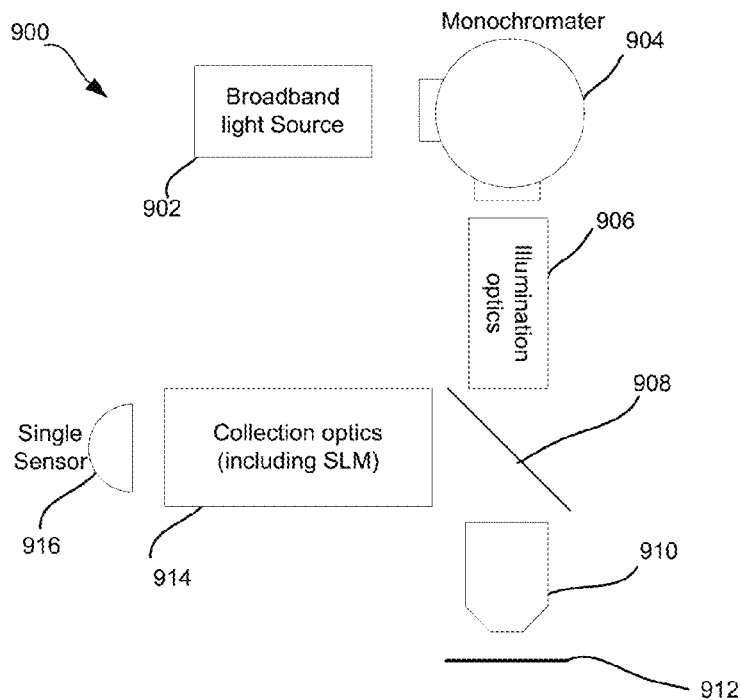
FIG. 9 is a diagrammatic representation of a compressive sensing system having a broadband light source and a monochromator to filter the input wavelength onto the wafer in accordance with another embodiment of the present invention.

FIG. 9 is a diagrammatic representation of a compressive sensing system 900 having a broadband light source 902 and one or more monochromators 904 to filter the input wavelength onto the wafer in accordance with another embodiment of the present invention. A monochromator 904 enables control over the wavelength and bandwidth of the incident radiation on the wafer. It also enables working in narrowband form, which may enable the use of certain technologies (e.g. the micro-mirror array technology by Fraunhofer in a Fourier setup, which is described in U.S. patent application Ser. No. 13/394,064). Additionally, the source 902 may be configured as a swept source, where wavelengths are swept through at high speeds (e.g. 1000 nm/sec). Also, one or more monochromators 904 can be used as filters for wavelengths down to 120 nm or less. This system configuration may also allow the light to be collected by a single sensor 916 that may be, but is not limited to, a Si detector or a photomultiplier. The latter provides very high sensitivity, including in the entire VUV-DUV-UV-VIS-IR spectral range, very low noise (could be used for single photon counting) and therefore requires very low levels of light, and is very fast, which may enable signal acquisition for the entire set of required signals within a timeframe that corresponds to a single camera frame or less in previous implementations of semiconductor metrology tools.

Figure 10:
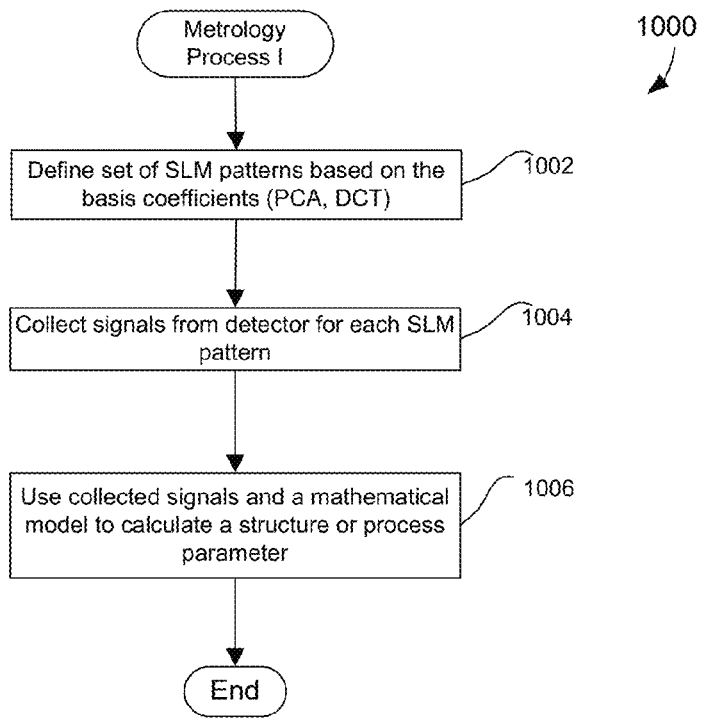
FIG. 10 is a flow chart illustrating a first metrology procedure using PCA coefficients in accordance with a first embodiment of the present invention.

In one implementation example, the coefficients of the PCA transformation (or the like) can be loaded directly into the SLM. FIG. 10 is a flow chart illustrating a first metrology procedure 1000 using PCA coefficients in accordance with a first embodiment of the present invention. In this case, a set of SLM patterns are defined based on the basis coefficients in operation 1002, for example, as determined by PCA or some other transformation and dimension reduction process. Signals from the sensor or spectrometer may be detected for each collection pattern (1004). That is, the value of the component is measured at the detector. For example, only K measurements are taken, where each SLM pattern represents the coefficients of a specific basis component. The collected signals from the detector and a mathematical model may then be used to calculate a structure or process parameter (e.g. Focus, Dose) in operation 1006.

The obtained components may be directly used for determining structure or process parameters, without reconstructing the pupil images. In general, a model is generated for correlating the measurements to a particular structure or process parameter. For instance, the spectra can be input to a model for predicting focus and dose based on the particular spectra.

Measurement of parameters of interest can also involve a number of algorithms. For example, optical interaction of the incident beam with the sample can be modeled using EM (electro-magnetic) solver and uses such algorithms as RCWA, FEM, method of moments, surface integral method, volume integral method, FDTD, and others. The target of interest can usually be modeled (parameterized) using a geometric engine, or in some cases, process modeling engine or a combination of both. The use of process modeling is described in "Method for integrated use of model-based metrology and a process model," by A. Kuznetsov et al. (pending U.S. 61/738,760, P4025). A geometric engine may be implemented, for example, in AcuShape software product of KLA-Tencor of Milpitas, Calif.

Collected data can be analyzed by a number of data fitting and optimization techniques an technologies including libraries, Fast-reduced-order models; regression; machine-learning algorithms such as neural networks, support-vector machines (SVM); dimensionality-reduction algorithms such as, e.g., PCA (principal component analysis), ICA (independent component analysis), LLE (local-linear embedding); sparse representation such as Fourier or wavelet transform; Kalman filter; algorithms to promote matching from same or different tool types, and others.

Collected data can also be analyzed by algorithms that do not include modeling, optimization and/or fitting e.g. provisional patent application 61/745,981, which is incorporated herein by reference, and as described herein.

Figure 11:
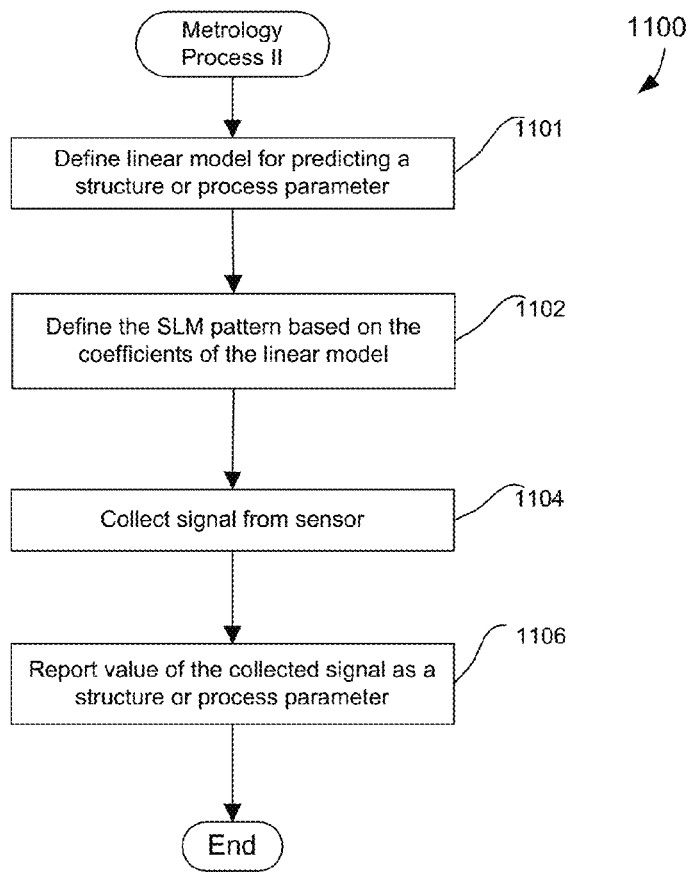
FIG. 11 is a flow chart illustrating a second metrology procedure in accordance with a second embodiment of the present invention.

FIG. 11 is a flow chart illustrating a second metrology procedure 1100 in accordance with a second embodiment of the present invention. Initially, the process or structure parameter can be predicted by using a linear model in operation 1101. The linear model is generally a weighted sum of signals for predicting a structure or process parameter for a particular type of structure. The model is generally trained to predict the particular parameter based on the image or signals obtained from a particular structure. For instance, the model multiplies each image pixel's intensity that is collected from the particular structure by a particular coefficient value, depending on what type of parameter is being predicted. The combined output signals from the model result in a value for the particular type of parameter that is being predicted by the model. A model parameter may include any structure value (e.g., CD, height, film, thickness, SWA, overlay, pitch walk, material dispersion and composition, etc.) or process value (dose, focus, etch time, deposition time, etc.) as described further herein.

In the illustrated process, an SLM pattern can be defined based on the coefficients of the linear model in operation 1102. That is, different pixel portions of the SLM may be configured to multiple different analog values (e.g., 0 to 1) with the corresponding intensities (or with other signal values) from different pupil image pixels so that the sensor receives a linear combination of weighted signals as output by the SLM. In the illustrated process 1100, a signal is collected from the sensor in operation 1104. In effect, the combined signals may be collected as a single signal at the sensor (e.g., single pixel camera). The collected signal represents the value of the particular parameter (e.g. Dose, Focus). Thus, the value of the collected signal can be reported as the value for the particular structure or process parameter in operation 1106.

This process 1100 may be repeated for any suitable type of parameter and associated model. Only one SLM pattern and one measurement are needed for each type of structure or process parameter. Additionally, it is unnecessary to reconstruct the pupil image. That is, this process for determining a structure or process parameter may be accomplished without reconstruction of the pupil image.

Figure 12:
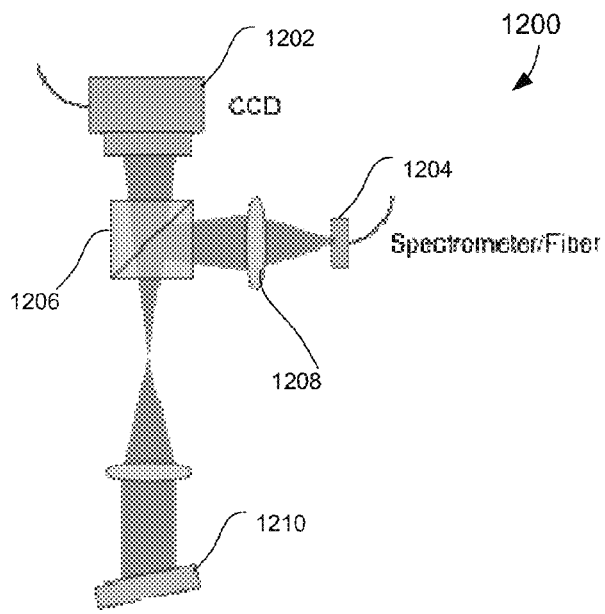
FIG. 12 shows a simplified diagram of an alternative collection system.

FIG. 12 shows a simplified diagram of an alternative collection system 1200. As shown, a beam splitter 1206 splits the output signal from the SLM 1210 into a first output signal that is focused by output optics 1208 onto a spectrometer 1204 and a second output signal that is received by CCD 1202. Such an arrangement would allow for simultaneous acquisition of angle-resolved and wavelength-resolved signals, which provides additional encoded information on CCD detector 1202, as compared to the system shown on FIG. 8A. Data from the CCD may be used for system calibration or to complement the spectrometer 1204 data. The CCD may also be used to perform data fitting that is not pixel-by-pixel (or by binned pixels), but by projecting the pupil onto an appropriate basis set.

Solving the under-determined linear equations above might include the use of optimization, minimization or other methods (e.g., $l_1$ minimization). Another option would be to use truncation of the base to reduce the set of equations into a determinate set. In this latter case the number of measurements should equal the truncation order. This method might introduce some error and the sufficient number of signals needs to be acquired in order to keep the residual error under the required spec.

Any suitable type of targets may be measured with metrology techniques and systems of the present invention as further described herein. In an alternative embodiment, asymmetric targets for overlay and focus may be utilized as described in U.S. Pat. No. 7,352,453 B2, which patent is incorporate herein by reference in its entirety.

In one embodiment, gray scale Digital Micromirror Device (DMD) operation mode is used. This allows for the projection of gray scale patterns on CCD camera. In some overlay/focus/dose applications, pixel weighting algorithms are used during data processing. Gray scale DMD imaging allows for hardware implementation of pixel weighting schemes.

Spatial light modulators are available in versions that spatially encode binary patterns (each pixel either reflects or transmits a well-defined small amount of light, the OFF state, or a well-defined large amount of light, the ON state) or encode a quasi-continuously spatially varying gray-scale distribution. An example of the binary type of device is the Texas Instruments Digital Micromirror Device (DMD). An example of the gray-scale type of device is a liquid crystal spatial light modulator or an appropriately spatially filtered Fraunhofer Institute MEMS spatial light modulator.

The above-described techniques can be utilized in any suitable application. For instance, fast measurements can be obtained and fed back to the lithographic tool for corrections to the process. Structure or process measurements can also be utilized for monitoring and improving etch, CMP or other processes. This control feedback may be implemented in real-time, with on-tool software.

Certain embodiments described above refer to reconstructing signals. In general, compressed sensing can be aimed at reconstructing signals that are of interest to the user such that geometrical and material parameters of a target may be deduced.

The use of SLM, DMD, or programmable illumination/collection also allows for optimizing measurements for any use case or parameter(s) of interest. For example, in the case of focus/dose metrology, DMD patterns can be preprogrammed to enable spectral signals in the detector that are particularly sensitive to focus or dose lithography parameter.

The acquired signals could be used to reconstruct an image or they might also be used to find parameters that could then directly be used to deduce the wafer or target characteristics. This could be done in methods such as signal response metrology (SRM). Several such technqiues are further described in U.S. Provisional App. No. 61/805,831, U.S. Provisional App. No. 61/814,191, and U.S. Provisional App. No. 61/864,573, which applications are incorporated herein by reference in their entirety.

Calibration techniques may be used to reduce the size of the required base for adequately representing the images or parameters with the acquired signals. Such calibrations might include (without limitation) mapping of the patterns to the measured signals in order to reduce the number of pixels for the analysis.

Certain embodiments allow measurements resolved by wavelength, angles, polarization state and field. In other words, measurement performance may be improved by increasing the information content and providing better sensitivity and reduced correlation. Small spot UV measurements are obtainable with certain embodiments to thereby result in, reduced resist damage since smaller spot size requires a smaller fraction of the light compared to other systems. Reduced SNR (signal-to-noise ratio) may be achieved by using a low SNR single pixel sensor. Reduced measurement time is also achievable with a low light budget. Certain embodiments also allow measurement of multiple targets or on-device measurements by resolving the field information.

Embodiments of the present invention are not limited by the systems and metrology techniques described herein. Example signals include, but are not limited to, any type of scatterometry, spectroscopic, ellipsometry, and/or reflectometry signals, including: $\Psi$, $\Delta$, Rs (complex reflectivity of the s polarization), Rp (complex reflectivity of the p polarization), Rs ($|r_s|^2$), Rp ($|r_p|^2$), R (unpolarized reflectivity), $\alpha$ (spectroscopic "alpha" signal), $\beta$ (spectroscopic "beta" signal), and functions of these parameters, such as $\tan(\Psi)$, $\cos(\Delta)$, ((Rs−Rp)/(Rs+Rp)), Mueller matrix elements ($M_{ij}$), etc. The signals could alternatively or additionally be measured as a function of incidence angle, detection angle, polarization, azimuthal angle of incidence, detection azimuthal angle, angular distribution, phase, or wavelength or a combination of more than one of these parameters. The signals could also be a characterization of a combination of signals, such as an average value of a plurality of any of the above described ellipsometry and/or reflectometry signal types. Other embodiments may use monochromatic or laser light sources where at least one of the signals may be obtained at a single wavelength, instead of multiple wavelengths. The illumination wavelengths could be any range, starting from X-ray wavelengths and going to far infra-red wavelengths.

A measurement site for the above described metrology techniques may include any suitable one or more structures of interest, such as a grating or film structure, which are expected to be smooth or uniform. For example, a grating that fills the entire measurement site would be expected to be uniform at different measurement locations across the measurement site area unless such grating is defective. Likewise, a film that fills the measurement site would be expected to have a same thickness (and uniformity) across the measurement site. Thus, this technique is applicable to regular structures, which may include films, 2D and 3D gratings, dot (or any other type) arrays, periodic structures, etc.

Any of the above-described metrology system may comprise one or more hardware configurations which may be used in conjunction with certain embodiments of this invention. Examples of such hardware configurations include, but are not limited to, the following: Spectroscopic ellipsometer (SE), SE with multiple angles of illumination, SE measuring Mueller matrix elements (e.g. using rotating compensator(s)), single-wavelength ellipsometers, beam profile ellipsometer (angle-resolved ellipsometer), beam profile reflectometer (angle-resolved reflectometer), broadband reflective spectrometer (spectroscopic reflectometer), single-wavelength reflectometer, angle-resolved reflectometer, imaging system, and scatterometer (e.g. speckle analyzer)

The hardware configurations can be separated into discrete operational systems. On the other hand, one or more hardware configurations can be combined into a single tool. One example of such a combination of multiple hardware configurations into a single tool is further illustrated and described U.S. Pat. No. 7,933,026, which patent is herein incorporated by reference in its entirety for all purposes. The wavelengths for the optical systems can vary from about 120 nm to 3 microns. The azimuth angle for the optical systems can also vary. For non-ellipsometer systems, signals collected can be polarization-resolved or unpolarized.

In many cases, multiple metrology tools are used for measurements on a single or multiple metrology targets. Several embodiments of multiple tool metrology are further described, e.g., in U.S. Pat. No. 7,478,019 by Zangooie et al, entitled "Multiple tool and structure analysis", which patent is incorporated herein by reference in its entirety for all purposes.

The illumination system of certain hardware configurations may include one or more light sources. The one or more light sources may generate light having only one wavelength (e.g., monochromatic light), light having a number of discrete wavelengths (e.g., polychromatic light), light having multiple wavelengths (e.g., broadband light), and/or light that sweeps through wavelengths, either continuously or hopping between wavelengths (e.g., tunable sources or swept sources). Examples of suitable light sources are: a white light source, an ultraviolet (UV) laser, an arc lamp or an electrode-less lamp, a laser sustained plasma (LSP) source, for example, those commercially available from Energetiq Technology, Inc. of Woburn, Mass., a supercontinuum source (such as a broadband laser source) such as those commercially available from NKT Photonics Inc. of Morganville, N.J., or shorter-wavelength sources such as x-ray sources, extreme UV sources, or some combination thereof. The illumination system may also include one or more filters (e.g., monochromator, thin film interference filter, etc.) for achieving specific wavelength ranges for light generated from a broadband source. The light source(s) may also be configured to provide light having sufficient brightness, which in some cases may be a brightness greater than about 1 W/(nm cm2 Sr). The metrology system may also include a fast feedback to the light source for stabilizing its power and wavelength. Output of the light source can be delivered via free-space propagation, or in some cases delivered via optical fiber or light guide of any type.

In turn, one or more detectors or spectrometers are configured to receive via a collection optical elements illumination reflected or otherwise scattered from the surface of the specimen. Suitable sensors include charged coupled devices (CCD), CCD arrays, time delay integration (TDI) sensors, TDI sensor arrays, photomultiplier tubes (PMT), and other sensors. Measured spectra or detected signal data (as a function of position, wavelength, polarization, azimuth angle, etc.) may be passed from each detector to the processor system for analysis.

The metrology tool may be designed to make many different types of measurements related to semiconductor manufacturing. For example, in certain embodiments the tool may measure spectra and determine characteristics of one or more targets, such as quality and defect quantity values, critical dimensions, overlay, sidewall angles, film thicknesses, process-related parameters (e.g., focus and/or dose). The targets can include certain regions of interest that are periodic in nature, such as for example gratings in a memory die. Targets can include multiple layers (or films) whose thicknesses can be measured by the metrology tool. Targets can include target designs placed (or already existing) on the semiconductor wafer for use, e.g., with alignment and/or overlay registration operations. Certain targets can be located at various places on the semiconductor wafer. For example, targets can be located within the scribe lines (e.g., between dies) and/or located in the die itself. In certain embodiments, multiple targets are measured (at the same time or at differing times) by the same or multiple metrology tools as described in U.S. Pat. No. 7,478,019. The data from such measurements may be combined. Data from the metrology tool may be used in the semiconductor manufacturing process, for example, to feed-forward, feed-backward and/or feed-sideways corrections to the process (e.g. lithography, etch) and therefore, might yield a complete process control solution.

As semiconductor device pattern dimensions continue to shrink, smaller metrology targets are often required. Furthermore, the measurement accuracy and matching to actual device characteristics increase the need for device-like targets as well as in-die and even on-device measurements. Various metrology implementations have been proposed to achieve that goal. For example, focused beam ellipsometry based on primarily reflective optics is one of them and described in the patent by Piwonka-Corle et al. (U.S. Pat. No. 5,608,526, "Focused beam spectroscopic ellipsometry method and system"). Apodizers can be used to mitigate the effects of optical diffraction causing the spread of the illumination spot beyond the size defined by geometric optics. The use of apodizers is described in the patent by Norton, U.S. Pat. No. 5,859,424, "Apodizing filter system useful for reducing spot size in optical measurements and other applications." The use of high-numerical-aperture tools with simultaneous multiple angle-of-incidence illumination is another way to achieve small-target capability. This technique is described, e.g. in the patent by Opsal et al, U.S. Pat. No. 6,429,943, "Critical dimension analysis with simultaneous multiple angle of incidence measurements."

Other measurement examples may include measuring the composition of one or more layers of the semiconductor stack, measuring certain defects on (or within) the wafer, and measuring the amount of photolithographic radiation exposed to the wafer. In some cases, metrology tool and algorithm may be configured for measuring non-periodic targets, see e.g. "The Finite Element Method for Full Wave Electromagnetic Simulations in CD Metrology Using Scatterometry" by P. Jiang et al (pending U.S. 61/830,536, K-T disclosure P4063) or "Method of electromagnetic modeling of finite structures and finite illumination for metrology and inspection" by A. Kuznetsov et al. (pending U.S. 61/761,146 or KT disclosure P4082). These applications are incorporated herein by reference in their entirety.

It should be recognized that the various steps described throughout the present disclosure may be carried out by a controller (e.g., 101 of FIG. 1), such as single processor system or, alternatively, a multiple processor system. Moreover, different subsystems of the system, such as the spectroscopic ellipsometer, may include a computer system suitable for carrying out at least a portion of the steps described herein. Therefore, the aforementioned description should not be interpreted as a limitation on the present invention but merely an illustration. Further, the one or more controller system may be configured to perform any other step(s) of any of the method embodiments described herein.

In addition, the controller system may be communicatively coupled to a detector system in any manner known in the art. For example, the controller system may be coupled to computing systems associated with the detector system. In another example, the detector system may be controlled directly by a single computer system coupled to the controller system.

The controller system of the metrology system may be configured to receive and/or acquire data or information from the subsystems of the system by a transmission medium that may include wireline and/or wireless portions. In this manner, the transmission medium may serve as a data link between the controller system and other subsystems of the system.

The controller system of the metrology system may be configured to receive and/or acquire data or information (e.g., measurement spectra or images, statistical results, reference or calibration data, training data, models, extracted features or transformation results, transformed datasets, curve fittings, qualitative and quantitative results, etc.) from other systems by a transmission medium that may include wireline and/or wireless portions. In this manner, the transmission medium may serve as a data link between the controller system and other systems (e.g., memory on-board metrology system, external memory, reference measurement source, or other external systems). For example, the controller system may be configured to receive measurement data from a storage medium (e.g., internal or external memory) via a data link. For instance, spectral results obtained using the detection system may be stored in a permanent or semipermanent memory device (e.g., internal or external memory). In this regard, the spectral results may be imported from on-board memory or from an external memory system. Moreover, the controller system may send data to other systems via a transmission medium. For instance, qualitative and/or quantitative results determined by processor system may be communicated and stored in an external memory. In this regard, measurement results may be exported to another system.

The controller system may include, but is not limited to, a personal computer system, mainframe computer system, workstation, image computer, parallel processor, or any other device known in the art. In general, the term "processor system" may be broadly defined to encompass any device having one or more processors, which execute instructions from a memory medium. Program instructions implementing methods such as those described herein may be transmitted over a transmission medium such as a wire, cable, or wireless transmission link. Program instructions may be stored in a computer readable medium (e.g., memory). Exemplary computer-readable media include read-only memory, a random access memory, a magnetic or optical disk, or a magnetic tape.

Computational algorithms are usually optimized for metrology applications with one or more approaches being used such as design and implementation of computational hardware, parallelization, distribution of computation, load-balancing, multi-service support, dynamic load optimization, etc. Different implementations of algorithms can be done in firmware, software, FPGA, programmable optics components, etc.

The data analysis and fitting steps may be used to pursue one of the following goals: measurement of quality, defect number, CD, SWA, shape, stress, composition, films, bandgap, electrical properties, focus/dose, overlay, generating process parameters (e.g., resist state, partial pressure, temperature, focusing model), and/or any combination thereof; modeling and/or design of metrology systems; and modeling, design, and/or optimization of metrology targets.

Certain embodiments of the present invention presented here generally address the field of semiconductor metrology and process control, and are not limited to the hardware, algorithm/software implementations and architectures, and use cases summarized above.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. For example, the techniques can be applied to other types of samples, beside semiconductor wafers, such as reticles. Accordingly, the present embodiments are to be considered as illustrative and not restrictive, and the invention is not to be limited to the details given herein.

What is claimed is:

1. A method of determining a structure or process parameter value of a target of interest on a semiconductor wafer, the method comprising:
   defining a plurality of collection patterns for a spatial light beam controller positioned at a pupil image plane of a metrology tool;
   for each collection pattern, collecting a signal from a sensor of the metrology tool, wherein each collected signal represents a combination of a plurality of signals that the spatial light beam controller samples, using each collection pattern, from a pupil image of the target of interest, wherein the collection patterns are selected so that the pupil image is reconstructable based on the collection patterns and their corresponding collection signals;
   analyzing the collected signal for each of the collection patterns to determine a structure or process parameter value for the target of interest;
   obtaining a representative set of pupil images from a plurality of test structures that were fabricated or simulated with known process variations;
   extracting basis images for a plurality of possible collection patterns that are most related to the known process variations from a large set, of basis images that are generated for the representative set of pupil images; and
   using the extracted basis images to define the collection patterns for the spatial light beam controller.

2. The method of claim 1, wherein the signal collected for each of the collection patterns is collected from a single point or pixel detector.

3. The method of claim 2, wherein each signal collected from the single point or pixel detector is a sum or average of a plurality of intensities that the spatial light beam controller samples from the pupil image.

4. The method of claim 1, further comprising:
   reconstructing the pupil image based on the collection patterns and their corresponding collection signals,
   wherein the pupil image of the target of interest is sparse when transformed to a particular domain of transformation elements $\Psi$, and
   wherein the pupil image can be represented by $\Psi\alpha$, with $\alpha$ being weights, and the pupil image is reconstructed by an $l_1$ optimization.

5. The method of claim 4, wherein the particular domain corresponds to a transform to a plurality of Zernike polynomial basis images.

6. The method of claim 4, wherein the particular domain corresponds to a MT (discrete Fourier transform), DCT (discrete cosine transform), or a Wavelet transform.

7. The method of claim 1, wherein the spatial light beam controller includes a plurality of pixels that are turned on or off for spatially sampling the pupil image to form each collection pattern.

8. The method of claim 1, wherein the spatial light beam controller includes a plurality of pixels that have a plurality of analog values for spatially sampling the pupil image to form each collection pattern.

9. The method of claim 1, further comprising:
   defining a plurality of illumination patterns for a second spatial light beam controller positioned at an illumination plane of the metrology tool.

10. The method of claim 9, further comprising:
    repeating the operations for defining, collecting, and reconstructing for each of a plurality of combinations of wavelength ranges, polarization states, and illumination patterns.

11. The method of claim 1, further comprising:
    repeating the operations for defining, collecting, and reconstructing for each of a plurality of combinations of wavelength ranges and polarization states.

12. The method of claim 1, wherein the structure or process parameter value is determined by a model for predicting a structure or process parameter value based on a plurality of collected signal values.

13. The method of claim 1, wherein the structure or process parameter value for the target of interest is determined without reconstructing the pupil image.

14. A semiconductor metrology system, comprising:
    an illuminator for generating illumination;
    illumination optics for directing the illumination towards a target of interest on a semiconductor wafer;
    collection optics for directing a plurality of signals from the particular structure to a sensor in response to the illumination, wherein the collection optics comprise a spatial light beam controller for controlling a spatial profile of a pupil image of the metrology system;
    the sensor for collecting the plurality of signals from the target of interest; and
    a controller configured for performing the following operations:
      defining a plurality of collection patterns for the spatial light beam controller;
      for each collection pattern, collecting a signal from the sensor of the metrology tool, wherein each collected signal represents a combination of a plurality of signals that the spatial light beam controller samples, using each collection pattern, from a pupil image of the target of interest, wherein the collection patterns are selected so that the pupil image is reconstructable based on the collection patterns and their corresponding collection signals; and analyzing the collected signal for each of the collection patterns to determine a structure or process parameter value for the target of interest;

obtaining a representative set of pupil images from a plurality of test structures that were fabricated or simulated with known process variations;

extracting basis images for a plurality of possible collection patterns that are most related to the known process variations from a large set of basis images that are generated for the representative set of pupil images; and using the extracted basis images to define the collection patterns for the spatial light beam controller.

15. The metrology system of claim 14, wherein the sensor is a single point or pixel detector.

16. The metrology system of claim 15, wherein each signal collected from the single point or pixel detector is a sum or average of a plurality of intensities that the spatial light beam controller samples from the pupil image.

17. The method of claim 14, wherein the controller is further configured for:

reconstructing the pupil image based on the collection patterns and their corresponding collection signals, wherein the pupil image of the target of interest is sparse when transformed to a particular domain of transformation elements $\Psi$, and wherein the pupil image can be represented by $\Psi\alpha$, with $\alpha$ being weights, and the pupil image is reconstructed by an $l_1$ optimization.

18. The metrology system of claim 17, wherein the particular domain corresponds to a transform to a plurality of Zernike polynomial basis images.

19. The metrology system of claim 17, wherein the particular domain corresponds to a DFT (discrete Fourier transform), DCT (discrete cosine transform), or a Wavelet transform.

20. The metrology system of claim 14, wherein the spatial light beam controller includes a plurality of pixels that are turned on or off for spatially sampling the pupil image to form each collection pattern.

21. The metrology system of claim 14, wherein the spatial light beam controller includes a plurality of pixels that have a plurality of analog values for spatially sampling the pupil image to form each collection pattern.

22. The metrology system of claim 14, further comprising:

a second spatial light beam controller positioned at an illumination plane of the metrology, wherein the controller is further configured for defining a plurality of illumination patterns for the second spatial light beam controller.

23. The metrology system of claim 22, wherein the controller is further configured for:

repeating the operations for defining, collecting, and reconstructing for each of a plurality of combinations of wavelength ranges, polarization states, and illumination patterns.

24. The metrology system of claim 14, wherein the controller is further configured for:

repeating the operations for defining, collecting, and reconstructing for each of a plurality of combinations of wavelength ranges and polarization states.

25. The metrology system of claim 14, wherein the structure or process parameter value is determined by a model for predicting a structure or process parameter value based on a plurality of collected signal values.

26. The metrology system of claim 14, wherein the structure or process parameter value for the target of interest is determined without reconstructing the pupil image.

27. The metrology system of claim 14, further comprises a monochromator to filter input wavelengths onto the target of interest.

28. The metrology system of claim 14, wherein the spatial light beam controller is a spatial light modulator, a liquid crystal device, a liquid crystal on Si (LCOS) device), and/or a set of masks.

29. A method of determining a structure or process parameter value of a target of interest on a semiconductor wafer, the method comprising:

defining one or more collection patterns for a spatial light beam controller positioned at a pupil image plane of a metrology tool, wherein each collection pattern is defined based on a plurality of coefficients of a model for predicting a corresponding structure or process parameter value for a target of interest;

for each collection pattern, collecting a signal from a sensor of the metrology tool, wherein each collected signal represents a combination of a plurality of signals that the spatial light beam controller samples, using each collection pattern, from a pupil image of the target of interest;

reporting a value of each collected signal for each of the collection patterns as a corresponding structure or process parameter value for the target of interest;

obtaining a representative set of pupil images from a plurality of test structures that were fabricated or simulated with known process variations;

extracting basis images for a plurality of possible collection patterns that are most related to the known process variations from a large set of basis images that are generated for the representative set of pupil images; and using the extracted basis images to define the collection patterns for the spatial light beam controller.

* * * * *